United States Patent [19]

Virtanen et al.

[11] Patent Number: 4,756,971
[45] Date of Patent: Jul. 12, 1988

[54] SURFACE TREATMENT AGENTS AND POLYMERS COMPRISING SUBSTITUTED PHENYL SILANES AND SILOXANES

[75] Inventors: Jorma A. Virtanen; Paavo K. J. Kinnunen; Arvo E. Kulo, all of Espoo, Finland

[73] Assignee: KSV-Chemicals Oy, Helsinki, Finland

[21] Appl. No.: 907,687

[22] PCT Filed: Dec. 20, 1985

[86] PCT No.: PCT/FI85/00102
§ 371 Date: Aug. 26, 1986
§ 102(e) Date: Aug. 26, 1986

[87] PCT Pub. No.: WO86/04063
PCT Pub. Date: Jul. 17, 1986

[30] Foreign Application Priority Data

Dec. 28, 1984 [FI] Finland ................... 845161

[51] Int. Cl.[4] .................... B32B 5/16; B32B 17/00; B01D 15/08; B01S 20/10
[52] U.S. Cl. .................... 428/405; 428/407; 428/409; 428/410; 428/429; 55/67; 210/656; 502/401; 502/407
[58] Field of Search .............. 428/405, 409, 410, 429; 210/656; 55/67; 502/401, 407; 556/465, 475, 478

[56] References Cited

U.S. PATENT DOCUMENTS

| | | | |
|---|---|---|---|
| 2,546,330 | 3/1951 | Barry et al. | 556/459 X |
| 2,556,462 | 6/1951 | Barry et al. | 556/481 |
| 2,626,270 | 1/1953 | Sommer | 260/448.2 |
| 3,312,727 | 4/1967 | Merker | 260/448.2 |
| 3,651,117 | 3/1972 | Bennett | 260/448.8 R |
| 3,722,181 | 3/1973 | Kirkland et al. | 55/67 |
| 3,853,726 | 12/1974 | Valmehielm et al. | 204/158 R |
| 3,899,328 | 8/1975 | Limburg | 260/448.8 A |
| 4,099,981 | 7/1978 | Mui et al. | 428/405 X |
| 4,164,509 | 8/1979 | Laufer | 556/400 |
| 4,242,227 | 12/1980 | Nestrick et al. | 55/67 X |
| 4,363,925 | 12/1982 | Acker et al. | 556/415 |
| 4,539,061 | 9/1985 | Sagiv | 427/407.1 X |

FOREIGN PATENT DOCUMENTS

| | | |
|---|---|---|
| 0028665 | 5/1983 | European Pat. Off. . |
| 834002 | 3/1952 | Fed. Rep. of Germany . |
| 1114492 | 4/1962 | Fed. Rep. of Germany . |
| 2132569 | 6/1975 | Fed. Rep. of Germany . |
| 2420389 | 4/1980 | Fed. Rep. of Germany . |
| 2930516 | 2/1981 | Fed. Rep. of Germany . |
| 1354357 | 5/1974 | United Kingdom . |
| 1078324 | 3/1984 | U.S.S.R. ................ 210/656 |

OTHER PUBLICATIONS

"Steric Hindrance in Highly-Substituted Organosilicon Compounds, I, the Reaction of Aryllithium Compounds with Some Chlorosilanes, Ethoxysilanes, and Related Compounds," Henry Gilman and G. N. Russell Smart, Journal of Organic Chemistry, vol. 15, 1950, pp. 720–740.

(List continued on next page.)

Primary Examiner—John E. Kittle
Assistant Examiner—Susan S. Rucker
Attorney, Agent, or Firm—Wolf, Greenfield & Sacks

[57] ABSTRACT

The invention concerns new compounds for making a hydrophilic surface lipophilic. The compounds have the general formula

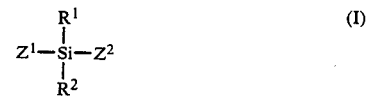

wherein $Z^1$ and $Z^2$ are independently chlorine, fluorine, bromine, alkoxy with not more than 6 carbon atoms, NH, $-NH_2$, $-NH_2'$, wherein R' is alkyl with 1 to 3 carbon atoms, $-SH$, $-CN$, $-N_3$ or hydrogen, and $R^1$ is

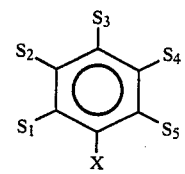

wherein each of the S-substituents, $S_1$, $S_2$, $S_3$, $S_4$ and $S_5$ are independently selected from the group consisting of hydrogen, alkyl with 1 to 4 carbon atoms, methoxy, ethoxy, and cyano, provided that at least one of the S-substituents is other than hydrogen and when there is a methyl or methoxy S-substituent then (i) at least two of the S-substituents are other than hydrogen, (ii) two adjacent S-substituents form with the phenyl nucleus a naphtalene or anthracene group, or three adjacent S-substituents form together with the phenyl nucleus a pyrene group, and X is the group $-(CH_2)_n-$, wherein n is 0 to 20, preferably 10 to 16, or the group

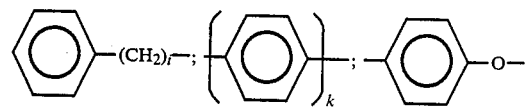

wherein i is 0 to 10 and k is 1 to 5, whereby, when n is not 0, i.e. X is a spacer group, the S-substituents, especially $S_3$, can also be phenoxy or biphenyl, and $R^2$ is equal to $Z^1$ or $R^1$, or is lower alkyl, lower alkenyl, phenyl, or phenyl substituted with lower alkyl or lower alkoxy. The novel compounds may be used as such for modifying the hydrophilic surface for a variety of purposes, such as for chromatographic purposes or for use in electronics, or the compound may be polymerized, optionally using as co-reactants known silanes, to form

11 Claims, No Drawings

OTHER PUBLICATIONS polymers especially well-suited for chromatographic purposes.

"Covalent Attachment of Arenes to $SNO_2$-Semiconductor Electrodes," Marye Anne Fox, Frederick J. Nobs, and Tamara A. Voynick, Journal of the American Chemical Society, Jun. 4, 1980, pp. 4029-4036.

"The Wettability of Ethyl- and Vinyltriethoxysilane Films Formed at Organic Liquid Silica Interfaces," Willard D. Bascom, Advances in Chemistry Series, vol. 87, 1968, pp. 38-41.

SURFACE TREATMENT AGENTS AND POLYMERS COMPRISING SUBSTITUTED PHENYL SILANES AND SILOXANES

This invention concerns an organosilicon compound for imparting lipophilic properties to a hydrophilic surface, such as that of glass, quartz, oxidized silicon, metal-metal oxide or of a plastic containing OH-and/or NH-groups. By means of the invention the physico-chemical characteristics, especially the adsorption characteristics of such a surface may be selectively modified and/or improved. According to one mode of the invention, the compound according to the invention may be polymerized, optionally using known silicon compounds, to form a silicon polymer, which may be applied by adsorption to a surface which advantageously has been pretreated according to the invention. Important fields of use of the compounds of this invention are in chromatography, both gas and liquid chromatography, especially gas chromatography, and in electronics.

It is known to treat surfaces of, e.g., glass, with organosilicon compounds or polymers in order to modify their hydrophilic characteristics, such as for chromatographic purposes, cf DE Nos. 834 002, 29 30 516, Advances in Chemistry Series, vol. 87 (1968), Bascom W. D. and GB No. 1,354,357. However, in these known methods, primarily aliphatic silanes have been used. In instances were aromatic silanes have been used, the phenyl substituent has either been unsubstituted or substituted with groups or atoms, notably halogen atoms, which do not provide the desired selectivity according to the invention. It is also known to form surface films containing more complicated substituted aromatic groups. However, rather than using the film-forming compound as such to make the film, the film is formed by building the desired molecule from smaller molecular moieties, starting from the substrate surface and proceeding therefrom in an outward direction by consecutively adding the required molecular moieties (Journal of American Chemical Society, vol. 102 (1980) no 12, p. 4029 to 4030).

It is an object of the invention to provide new organosubstituted silanes, containing as a substituent a phenyl group which is further substituted, so as to provide compounds by means of which the properties of the treated surface may be tailor-made in a highly selective manner. This object is achieved by selectively choosing such substituents on the phenyl group(s) in the silane, which are able to actively participate in intermolecular forces, such as in the formation of charge-transfer complexes.

The organo-substituated silane according to the invention is represented by the general formula

wherein $Z^1$ and $Z^2$ each is independently chlorine, fluorine, bromine, alkoxy with not more than 6 carbon atoms, NH, $-NH_2$, $-NR_2'$, wherein R' is alkyl with 1 to 3 carbon atoms, $-SH$, $-CN$, $-N_3$ or hydrogen, and $R^1$ is

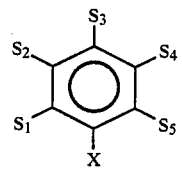

wherein each of the S-substituents, $S_1$, $S_2$, $S_3$, $S_4$ and $S_5$ are independently selected from the group consisting of hydrogen, alkyl with 1 to 4 carbon atoms, methoxy, ethoxy, and cyano, provided that at least one of the S-substituents is other than hydrogen and when there is a methyl or methoxy S-substituent then (i) at least two of the S-substituents are other than hydrogen, (ii) two adjacent S-substituents form with the phenyl nucleus a naphtalene or anthracene group, or (iii) three adjacent S-substituents form together with the phenyl nucleus a pyrene group, and X is the group $-(CH_2)_n-$, wherein n is 0 to 20, preferably 10 to 16 when n is not 0, i.e., X is a spacer group, the S-substituents, especially $S_3$, can also be phenoxy and biphenyl, or one of the following groups

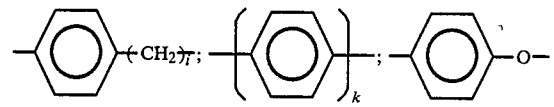

and $R^2$ is equal to $Z^1$ or $R^1$, or is lower alkyl, lower alkenyl, phenyl, or phenyl substituted with lower alkyl or lower alkoxy.

The term "lower" in connection with groups or compounds, means from 1 to 7 and, preferably from 1 to 4, carbon atoms.

Especially advantageous compounds according to the invention are obtained when $R^1$ is one of the following groups

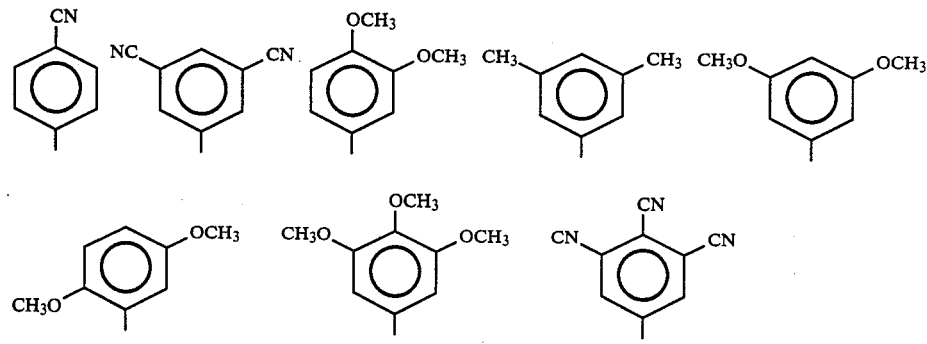

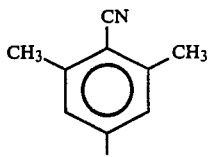
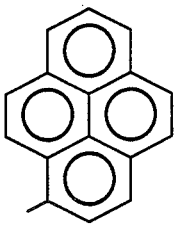

which groups R¹ are attached directly to the silicon atom or to one of the following spacer groups X

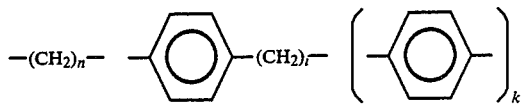

wherein i is 1 to 10 and k is 1 to 5.

The compounds according to the invention are thus silanes containing at least one group Z, which can form a chemical bond with a hydrophilic group of the surface to be treated, and one or two selectively substituted phenyl groups.

According to the invention, the adsorption characteristics of the surface thus treated may be modified and/or improved. More specifically the surface may be modified in a selective manner by using the specific substituents on the phenyl group as defined above. Surfaces are thus obtained which are well-suited to a variety of purposes, such as for chromatographic purposes, or which have specific electrical properties and are suitable for use in electronic applications, and/or which may be further treated, for example by adsorbing thereon a further layer, e.g., obtained by polymerizing the compounds (I).

The most important forces prevailing between non-ionic molecules stem from hydrogen bonds and dipole-dipole interactions. In certain instances, the formation of charge-transfer complexes is prevalent. Compared to these forces the Van der Waals forces are weak. However, in certain instances the only forces between molecules are the Van der Waals forces.

As mentioned above, surfaces have previously been coated for chromatographic purposes with compounds such as methyl-, octadecyl- and phenylsiloxanes, the interaction of which with the compounds to be fractionated is weak. An essential characteristic of the invention is that the relationship between these different forces can be selectively regulated as compared to the use of plain alkyl or phenyl groups. The manner of regulating according to the invention is illustrated in the following.

Hydrogen bonding acceptor properties are enhanced by the introduction into the phenyl group of, e.g., methoxy or cyano groups. In the case of two methoxy groups the following isomers are formed

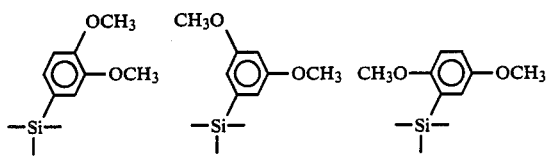

In these compounds the mutual distances between the oxygen atoms are 2.8 Å, 4.8 Å, and 5.6 Å. Thus if a compound which is to interact with a surface treated with a dimethoxyphenyl compound contains two active hydrogen atoms at a predetermined mutual distance, the one dimethoxy-phenyl isomer is chosen for surface treatment in which the distance between the dimethoxy groups is suitable, i.e., best corresponds to that between the hydrogen atoms, resulting in a strong interaction.

Also dipole-dipole interactions may be enhanced by the use of methoxy and cyano groups. As the dipole moments of structural isomers vary considerably, the chromatographic separation of isomers can be facilitated.

Charge-transfer donor characteristics are enhanced by the use of alkyl or alkoxy groups, especially methyl and methoxy groups. On the other hand, charge-transfer acceptor characteristics are enhanced by the use of cyano groups. Polycyclic aromatic hydrocarbons being charge-transfer donors form together with cyano substituted aromatic groups charge-transfer complexes. By varying the number and position of the cyano groups, the stability of the complexes may be varied, which fact finds applicability for example in chromatography as well as in electronics.

Especially in connection with gas chromatography the thermal stability of the surface layer is important. The bond between an aromatic group and the silicon atom is strong. On the other hand, it is occasionally of advantage that the active group not be close to the substrate surface. Both of these objects may be achieved by using a spacer group compound according to the invention which comprises a p-phenylene-methyl- or a poly-p-phenylene group as follows

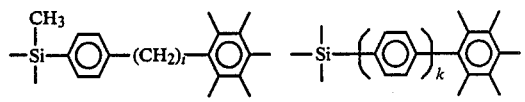

The poly-p-phenylene structure is of importance also in electronic applications, especially in cases where the substrate is a metal-metal oxide as it allows for easy electron transfer between the treated metal surface and a second film adsorbed onto the treated surface. As a specific example may be mentioned treating an indium-tin oxide covered glass surface with a poly-p-phenylene silane compound containing in the terminal phenyl ring a cyano group, onto which treated surface a pyrene group containing phosphoglycerol film may be adsorbed, the cyano group and the pyrene group forming a charge-transfer complex, as stated above.

As mentioned above, according to one mode of the invention, in order to enhance or modify the adsorption characteristics of a surface, especially useful for gas chromatography purposes, onto a surface optionally treated with a silane according to the invention may be adsorbed a polymerized film of the same or of a similar silane compound containing the active phenyl groups defined in the formula I, the polymerized silane having the formula

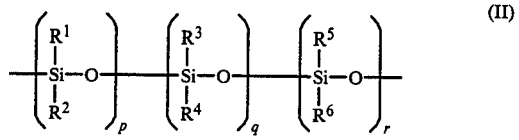

wherein $R^1$ and $R^2$ have the meanings defined above, $R^3$ to $R^6$ are independently lower alkyl, lower alkenyl, phenyl or lower alkyl-phenyl and $p \geq 1$, and q and $r \geq 0$. The groups $R^1$ and $R^2$ may be the same as or different from the corresponding groups used in the surface treatment step. The groups R in the polymer are naturally chosen according to the end use of the surface in question. The preparation of the polymers is conventional, and known to a person skilled in the art.

As also mentioned above, another important field of use of the invention is in electronics, especially in applications where surfaces treated according to the invention are used together with films of Langmuir-Blodgett type, for example in photo or sun cells, micro circuits, etc. Thus for example silane compounds with substituents having electron acceptor characteristics, for example cyano groups, may be used for treating a surface. Onto such a surface exhibiting electron acceptor characteristics a film containing donor groups, for example alkyl or alkoxy groups, of the Langmuir-Blodgett type may be applied. Electron transfer between these layers may be initiated with external means, for example using a voltage potential or light. The donor groups may naturally be included in the surface treatment agent, whereby on the treated surface a layer exhibiting acceptor characteristics is applied.

The silane compounds according to the invention are novel and they may be prepared using processes equivalent to processes known in the art. A suitable method for preparing these compounds is the Grignard reaction, whereby one mole of a Grignard reagent $R^1$—Mg Br, prepared in a known manner, is reacted with one mole of a compound having the formula $R^2Si(Z^1)_2Z^2$, in which formulas the symbols have the above meanings. An alternative mode of preparing the compounds of the invention, wherein X is a p-phenylene containing spacer group, comprises forming in a first step in a manner described above the corresponding p-Br-substituted silane compound, Br-X-$(R^2)SiZ^1Z^2$ wherein the Z-substituents have the above meanings, but may not be halogen, and thereafter forming its zinc derivative Br-Zn-X-$(R^2)SiZ^1Z^2$ which in the presence of a suitable Pt-catalyst together with the compound

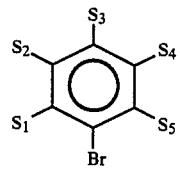

gives the desired compound.

The following examples illustrate the invention.

EXAMPLE I 117 g (0.63 moles) of 5-bromo-1,3-dimethyl-benzene was dissolved in anhydrous tetrahydrofuran. This solution was slowly added to a reaction flask wherein 17.0 g (0.70 moles) of magnesium shavings were stirred in anhydrous tetrahydrofuran. Nitrogen gas was used as a protective gas in the flask. After the addition the solution was boiled for a further half hour. The cooled solution was slowly added to a vigorously stirred solution containing 250 ml (2.13 moles) of methyl-trichlorosilane in anhydrous tetrahydrofuran. During the addition the temperature was kept at 0° to 10° C. After the addition the solution was stirred for a further 2 hours at 20° C.

From the reaction mixture a major part of the solvent and unreacted methyl-trichlorosilane were removed under reduced pressure. From the pulpy residue the product was extracted with n-hexane.

The n-hexane extract was concentrated and the product isolated by vacuum distillation.

The product, (3,5-dimethyl-phenyl)-methyl-dichlorosilane, exhibited a boiling point of 67° C./0.12 mbar. Its NMR-spectrum confirmed its structure. Its purity was determined using gas chromatography.

EXAMPLE II 202 g (0.93 moles) of 4-bromo-1,2-dimethoxy-benzene was dissolved in anhydrous tetrahydrofuran. This solution was slowly added to a flask wherein 24.3 g (1.00 moles) of magnesium was stirred in anhydrous tetrahydrofuran. Nitrogen was used as a protective gas in the flask. After the addition, the solution was stirred for a further half hour. The cooled reaction mixture was slowly added to a vigorously stirred solution containing 370 ml (3.14 moles) of methyl-trichlorosilane in anhydrous tetrahydrofuran. During the addition the temperature was kept at 0° to 10° C. After the addition the solution was stirred for 2 hours at 20° C.

From the reaction mixture a major part of the solvent and unreacted methyl-trichlorosilane were removed. The product was extracted from the pulpy residue with a mixture of n-hexane and anhydrous ethylether.

The extract was concentrated and thereto was added 390 g (3.7 moles) of trimethylortoformate. After about a week the mixture was distilled under reduced pressure. The crude product was distilled under vacuum.

The product, (3,4-dimethoxyphenyl)-methyl-dimethoxy-silane, exhibited a boiling point of 113° C./0.4 mbars. Its NMR-spectrum confirmed its structure. Its purity was determined using gas chromatography.

In the same way as described in the Examples I and II the following compounds may be prepared:
3-(3,5-dimethoxyphenyl)-propyl-trichloro-silane,
6-(1-pyrenyl)-hexyl-methyl-dimethoxy-silane,
16-(2,5-dimethoxyphenyl)-hexadecyl-trimethoxy-silane,
4-quaterphenyl-trimethoxy-silane, and
4-/4'-(phenoxy)-phenoxy/-phenyl-methyl-dichloro-silane.

EXAMPLE III 141 g (0.67 moles) of 4-bromo-2,6-dimethyl-benzonitrile was dissolved in a mixture of anhydrous tetrahydrofuran and methyldimethoxychlorosilane. This solution was slowly added to a flask wherein 36.5 g (1.5 moles) of magnesium was stirred in anhydrous tetrahydrofuran. In the flask nitrogen was used as a protective gas and the reaction temperature was 10° to 35° C. After about 20 hours a major part of the solvent and unreacted methyldimethoxychlorosilane were removed from the reaction mixture under reduced pressure. The product was extracted from the pulpy residue with a mixture of n-hexane and anhydrous ethylether.

The extract was concentrated and the product isolated by vacuum distillation. The crude product was purified by means of vacuum distillation.

The product, (3,5-dimethyl-4-cyano-phenyl)-methyl-dimethoxysilane, exhibited a boiling point of 120° C./0.4 mbars. Its structure was confirmed with NMR and its purity determined with gas chromatography.

The purity of the products according to Examples I, II and III was over 95%.

In the same way as described in the Example III, the following compounds may be prepared:
(3,5-dicyano-phenyl)-phenyl-dimethoxy-silane, and
(3',5'-dicyano-biphenyl)-methyl-dimethoxy-silane.

EXAMPLE IV

A silicon polymer containing 10% of 3,5-dimethylphenyl groups was prepared in the following manner.

In a flask using nitrogen as a protective gas, at 0° C., 3.000 g (0.01369 moles) of (3,5-dimethyl-phenyl)-methyl-dichlorosilane, 7.022 g (0.05446 moles) of dimethyldichlorosilane and 0.0897 g (0.0006 moles) of methyltrichlorosilane were mixed and to this flask was slowly added a 6N ammonia solution. The product was extracted into ethylether, and the ether extract washed with water and dried with anhydrous calcium sulfate.

The polymerization was carried out by evaporating the ethylether and to the residue 0.1% of tetramethylammoniumhydroxide was added. The mixture was stirred under nitrogen gas at 100°–120° C. and the viscous product for a further 20 minutes at 140° C. to destroy the catalyst. The silanol groups in the product were capped by treatment with hexamethyldisilazane for 8 hours at 80° to 100° C.

The low molecular compounds were removed by dissolving the product in ethylether and precipitating the polymer by the addition of methanol or a water-methanol mixture. The steps of dissolution and precipitation were repeated several times. The solvent residues were removed in a nitrogen stream at 120° C.

From the product a silica capillary column was prepared, using as a substrate a commercial fused silica capillary, onto the inside surface of which after treatment according to the invention, a film of the polymerized silicon compound was adsorbed. The characteristics of the column were tested using a Grob-test mixture.

EXAMPLE V

A silicon polymer containing 25% of 3,4-dimethoxyphenyl groups was prepared in the following manner.

In a flask under a nitrogen atmosphere, at 20° C., 4.846 g (0.020 moles) of (3,4-dimethoxyphenyl)-methyl-dimethoxysilane, 2.188 g (0.0182 moles) of dimethyl-dimethoxysilane, 0.0545 g (0.00040 moles) of methyl-trimethoxysilane and 0.138 g (0.00053 moles) of 1,3,5-trivinyl-1,3,5-trimethyl-cyclotrisiloxan were mixed for 50 hours with 7 ml of acetonitrile and 7 ml of water. To the reaction mixture water was added and the product extracted with dichloromethane.

The product was polymerized and tested as in Example IV.

EXAMPLE VI

A silicon polymer containing 5.5% of 3,5-dimethyl-4-cyano-phenyl groups was prepared in the following manner.

In a flask 2.350 g (0.010 moles) of (3,5-dimethyl-4-cyanophenyl)-methyldimethoxy-silane and 9.620 g (0.080 moles) of dimethyldimethoxysilane were mixed with 7 ml of acetonitrile and 7 ml of water at 20° C. for 50 hours. To the reaction mixture water was added and the product was extracted with dichloromethane.

The product was polymerized and tested as in Example IV.

In the following Table the retention times for the polymers of Examples IV, V and VI with respect to certain listed test compounds are given. For comparison purposes a commercial column SE-54 was used.

From the results obtained it can be seen that for a number of test compounds the retention times are greatly increased as compared to those of the standard column, which naturally is of advantage in certain applications. More important, however, is the fact that by using different active groups on the phenyl nucleus, the retention time for any specific compound may be varied, thus allowing for the tailor-making of columns for e.g. gas chromatography for specific applications.

TABLE

| Retention times (RT) and relative retention time (RRT) in minutes | | | | | | | | |
|---|---|---|---|---|---|---|---|---|
| | SE-54 | | Ex. IV | | Ex. V | | Ex. VI | |
| Test compound | RT | RRT | RT | RRT | RT | RRT | RT | RRT |
| D=2,3-butanediol | 2.35 | 1.00 | 3.32 | 1.41 | 5.50 | 2.34 | 4.30 | 1.83 |
| C$_{10}$=n-decane | 5.25 | 1.00 | 6.25 | 1.19 | 4.35 | 0.83 | 4.75 | 0.90 |
| C$_{11}$=n-undecane | 6.82 | 1.00 | 7.90 | 1.16 | 5.82 | 0.85 | 6.26 | 0.92 |
| ol=1-octanol | 6.35 | 1.00 | 7.65 | 1.20 | 8.20 | 1.29 | 7.60 | 1.20 |
| al=nonanal | 6.90 | 1.00 | 8.30 | 1.20 | 8.10 | 1.17 | 7.80 | 1.13 |
| P=2,6-dimethyl phenol | 7.10 | 1.00 | 8.65 | 1.22 | 10.53 | 1.48 | 9.35 | 1.32 |
| A=2,6-dimethyl aniline | 7.96 | 1.00 | 9.73 | 1.22 | 10.80 | 1.36 | 9.72 | 1.22 |
| S=2-ethyl hexanoic acid | 7.20 | 1.00 | 8.45 | 1.17 | 10.83 | 1.50 | — | — |
| am=dicyclohexyl amine | 11.75 | 1.00 | 13.26 | 1.13 | 12.06 | 1.03 | 1.90 | 1.01 |
| E$_{10}$=methyl decanoate | 10.28 | 1.00 | 11.62 | 1.13 | 10.95 | 1.07 | 10.60 | 1.03 |
| E$_{11}$=methyl undecanoate | 11.68 | 1.00 | 13.06 | 1.12 | 12.34 | 1.06 | 12.00 | 1.03 |
| E$_{12}$=methyl dodecanoate | 13.05 | 1.00 | 14.45 | 1.10 | 13.63 | 1.04 | 13.30 | 1.02 |
| Stationary phase composition | | | | | Phase layer | | Column I.D. | Length |
| SE-54 phenyl 5%, vinyl 1% | | | | | 0.25 μm | | 0.20 mm | 25 m |
| Ex. IV 3,5-dimethyl phenyl 10% | | | | | 0.25 μm | | 0.20 mm | 25 m |
| Ex. V 3,4-dimethoxy phenyl 25%, vinyl 2% | | | | | 0.20 μm | | 0.20 mm | 25 m |
| Ex. VI 3,5-dimethyl-4-cyanophenyl 5.5% | | | | | 0.20 μm | | 0.20 mm | 25 m |

We claim:

1. A substrate having a hydrophilic surface such as glass, quartz, oxidized silicon, metal-metal oxide, or a plastic containing OH- and/or NH-groups, the hydrophilic surface of the substrate having been treated with a compound of the general formula:

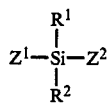 (I)

or a polymeric siloxane prepared from the compound of formula (I), wherein:

$Z^1$ and $Z^2$ are independently selected from the group consisting of chlorine, flourine, bromine, alkoxy with not more than 6 carbon atoms, NH, —$NH_2$, —$NR'_2$, where R' is alkyl with 1 to 3 carbon atoms, SH, —CN, —$N_3$, and hydrogen;

$R^1$ is a compound having the general formula

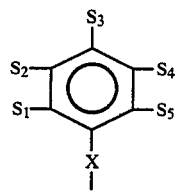

wherein:
the S-substituents, $S_1$, $S_2$, $S_3$, $S_4$ and $S_5$ are independently selected from the group consisting of hydrogen, alkyl with 1 to 4 carbon atoms, methoxy, ethoxy, and cyano, provided that
(a) at least one of the S-substituents is other than hydrogen;
(b) when there is a methyl or methoxy S-substituent then (i) at least two of the S-substituents are other than hydrogen, (ii) two adjacent S-substituents form with the phenyl nucleus a naphtalene or an anthracene group, or (iii) three adjacent S-substituents form with the phenyl nucleus a pyrene group;

X is selected from the group consisting of
(a) —$(CH_2)_n$— wherein n is 0 to 20, and when n is not 0 the S-substituents can also be phenoxy and biphenyl;
(b)

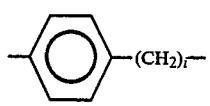

wherein i is 0 to 10;
(c)

wherein k is 1 to 5; and (d)

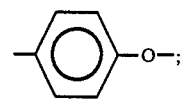

and
$R^2$ is the same as $Z^1$ or $R^1$ or is selected from the group consisting of lower alkyl, lower alkenyl, phenyl, and phenyl substituted with lower alkyl or lower alkoxy.

2. Substrate according to the claim 1 having applied thereto a Langmuir-Blodgett film.

3. Substrate according to the claim 1 to be used for chromatography, especially gas chromatography, wherein to the surface is applied a polymeric siloxane having the formula:

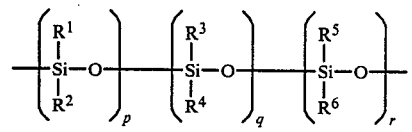

wherein $R^1$ and $R^2$ have the same meanings previously defined and $R^3$ to $R^6$ are independently selected from the group consisting of lower alkyl, lower alkenyl, phenyl, and lower alkyl-phenyl, and $p \geq 1$, and q and $r \geq 0$.

4. Substrate according to the claim 2, characterized in that for the surface treatment the compound of formula I has a substituent in the $R^1$ group with electron acceptor properties, and the Langmuir-Blodgett film contains groups with electron donor characteristics.

5. Substrate according to the claim 4, characterized in that the group with electron acceptor properties is cyano and the group with electron donor characteristics is selected from the group consisting of alkyl and alkoxy.

6. Substrate according to the claim 2, characterized in that for the surface treatment the compound of formula I has a substituent in the $R^1$ group with electron donor characteristics and the Langmuir-Blodgett film contains groups with electron acceptor characteristics.

7. Substrate according to the claim 6, characterized in that the group with electron acceptor properties is cyano and the group with electron donor characteristics is selected from the group consisting of alkyl and alkoxy.

8. Substrate according to the claim 2, characterized in that for the treatment of a conductive surface, the compound of formula I contains an aromatic spacer group X for providing mediating electron transfer between the surface and the Langmuir-Blodgett film applied thereon.

9. Substrate according to claim 8, characterized in that the group X is a poly-p-phenylene group.

10. Substrate according to claim 1, characterized in that when n is not 0, $S_3$ is selected from the group consisting of phenoxy and biphenyl.

11. Substrate according to claim 1, characterized in that n is 10 to 16.

* * * * *